United States Patent [19]

Bagshawe et al.

[11] Patent Number: 5,632,990
[45] Date of Patent: May 27, 1997

[54] TREATMENT FOR TUMORS COMPRISING CONJUGATED ANTIBODY A5B7 AND A PRODRUG

[75] Inventors: Kenneth D. Bagshawe; Gordon T. Rogers; Surinder K. Sharma, all of London, United Kingdom

[73] Assignees: Cancer Research Campaign Tech. Ltd.; Zeneca Ltd., both of London, England

[21] Appl. No.: 313,866

[22] Filed: Sep. 28, 1994

Related U.S. Application Data

[62] Division of Ser. No. 642,301, Dec. 21, 1990, abandoned.

[30] Foreign Application Priority Data

Apr. 22, 1988 [GB] United Kingdom ............... 8809616

[51] Int. Cl.$^6$ ..................... C12N 15/00; C12P 21/00; A61K 39/395
[52] U.S. Cl. ..................... 424/178.1; 530/391.1; 530/388.8; 424/180.1; 424/193.1; 424/94.1; 435/174
[58] Field of Search ............... 530/391.1, 388.8; 424/178.1, 180.1, 193.1, 94.1; 435/174

[56] References Cited

U.S. PATENT DOCUMENTS

| | | |
|---|---|---|
| 4,185,111 | 1/1980 | Ducep et al. |
| 4,564,675 | 1/1986 | Kurabayashi et al. |
| 4,675,187 | 6/1987 | Konishi et al. |
| 4,762,707 | 8/1988 | Jansen et al. |
| 4,975,278 | 12/1990 | Senter et al. ............... 424/94.3 |

FOREIGN PATENT DOCUMENTS

| | | |
|---|---|---|
| 1216791 | 1/1987 | Canada. |
| 089880 | 9/1983 | European Pat. Off.. |
| 0142905 | 5/1985 | European Pat. Off.. |
| 140728 | 5/1985 | European Pat. Off.. |
| 186551 | 7/1986 | European Pat. Off.. |
| 287353 | 10/1988 | European Pat. Off.. |
| WO87/03205 | 6/1987 | WIPO. |
| WO88/07378 | 10/1988 | WIPO. |

OTHER PUBLICATIONS

Radford Infection and Immunity vol. 56 No. 4, Apr. 1988 921–925.
Searle et al. Br. J. Cancer 1986 (53) 377–384.
Oshaud et al. Immunology Today vol. 11 No. 6, 1990 (193).
Waldman Science vol. 252 1991 p. 1657.
Harris TibTech 1993 vol. 11 p. 42.
Reichman Nature vol. 332 1988 p. 323.
Hird et al Genes and Cancer Ed. By Carney and Sikore 1990.
Harwood et al., "Mapping epitope characteristics on carcinoembryonic antigen", Br. J. Cancer 54: 75–82 (1986).
Pedley et al., "Relationship between tumour size and uptake of radiolabelled anti–CEA in a colon tumour xenograft", Eur. J. Nucl. Med 13: 197–202 (1987).
Blakey et al., "Anti–tumour effects of an antibody–carboxypeptidase G2 conjugate in combination with phenol mustard prodrugs", Br. J. Cancer 72: 1083–1088 (1995).
Sharma et al., "Pharmacokinetics of monoclonal anti–CEA antibody–enzyme (A5B7–F(ab')$_2$–CPG2) conjugate in Adept." Antibody Immunoconjugates and Radiopharmaceuticals 62:16'(1995).
Blakey et al., "Comparison of the Cellular Internalization of Antibodies Used Either as Immunotoxins or in Adept", Cell Biophysics 24/25: 175–183 (1994).
Bagshawe et al., "Antibody directed enzyme prodrug therapy: a pilot–scale clinical trial", Tumor Targeting 1: 17–29 (1995).
"Monoclonal and Polyclonal Antibodies and Kits", p. 68 of a catalogue of Dako Ltd. (1991).
Nap et al., "Specificity and Affinity of Monoclonal Antibodies against Carcinoembryonic Antigen", Cancer Research 52: 2329–2339 (1992).
Editors: Carl A.K. Borrebaeck and James W. Larrick, "Therapeutic Monoclonal Anitbodies", pp. 17–141 (1990).
I. Hellström et al., "Monoclonal Mouse Antibodies Raised against Human Lung Carcinoma", Cancer Research, 46, pp. 3917–3923 (Aug. 1986).
G. W. Philpott et al., "Affinity Cytotoxicity of Tumor Cells with Antibody–Glucose Oxidase Conjugates, Peroxidase, and Arsphenamine", Cancer Research, 34, pp. 2159–2164 (Sep. 1974).

I. Hellström et al., "Monoclonal Antibodies to Two Determinants of Melanoma–Antigen p97 Act Synergistically in Complement–Dependent Cytotoxicity", *The Journal of Immunology*, 127(1), pp. 157–160 (Jul. 1981).

V. J. Stella et al., "Prodrugs: A Chemical Approach to Targeted Drug Delivery", *Directed Drug Delivery*, pp. 247–267 (1985).

T. Nishiyama et al., "Antineoplastic Effects in Rats of 5–Fluorocytosine in Combination with Cytosine Deaminase Capsules", *Cancer Research*, 45, pp. 1753–1761 (Apr. 1985).

D. E. V. Wilman, "Prodrugs in Cancer Chemotherapy", *Biochemical Society Transactions*, 14, pp. 375–382, (615th Meeting, Belfast 1986).

P. J. O'Dwyer et al., *The New England Journal of Medicine*, 312, pp. 692–700 (Mar. 14th, 1985).

A. P. Albino et al., "Heterogeneity of Surface Antigen and Glycoprotein Expression of Cell Lines Derived from Different Melanoma Metastases of the Same Patient", J. Exp. Med., 154, pp. 1764–1778 (Dec. 1981).

R. Arnon et al., "In Vitro and In Vivo Efficacy of Conjugates of Daunomycin with Anti–Tumor Antibodies", *Immunological Rev.*, 62, pp. 5–27, (1982).

K. D. Bagshawe, "Antibody Directed Enzymes Revive Anti–Cancer Prodrugs Concept", *Br. J. Cancer*, 56, pp. 531–532 (Nov. 1987).

K. D. Bagshawe, "A Novel Approach to Prodrug Activation Using a Monoclonal Antibody Conjugated to Carboxypeptidase G2", from the Third International Conference on Monoclonal Antibody Immunoconjugates for Cancer, Abstract #43, p. 70 (San Diego, Feb. 4–6, 1988).

R. W. Baldwin et al., "Design and Therapeutic Evaluation of Monoclonal Antibody 791T/36–Methotrexate Conjugates" *Monoclonal Antibodies and Cancer Therapy*, pp. 215–231 (Alan R. Liss, Inc. 1985).

R. W. Baldwin et al., "Monoclonal Antibodies in Cancer Treatment", *Lancet*, pp. 603–605 (Mar. 15, 1986).

R. W. Baldwin et al. "Monoclonal Antibody Drug Conjugagates for Cancer Therapy", *Monoclonal Antibodies in Cancer: Advances in Diagnosis and Treatment*, Jack A. Roth (ed)., pp. 215–257 (Futura Publishing Co., 1986).

J. P. Brown et al., "Structural Characterization of Human Melanoma–Associated Antigen p97 with Monoclonal Antibodies", *J. Immunology*, 127(2), pp. 539–546, (Aug. 1981).

E. A. Clark et al., "Role of the Bp35 Cell Surface Polypeptide in Human B–Cell Activation", *Proc.Natl.Acad.Sci.*, 82, pp. 1766–1770 (Mar. 1985).

S. T. Crooke et al. (eds.) *Anthracyclines: Current Status and New Developments*, Academic Press, cover pages and table of contents, (New York, 1980).

R. A. DeWeger et al., "Eradication of Murine Lymphoma and Melanoma Cells by Chlorambucil–Antibody Complexes", *Immunological Rev.*, 62, pp. 29–45 (1982).

M. J. Embleton et al., "Antibody Targeting of Anti–Cancer Agents", *Monoclonal Antibodies for Cancer Detection and Therapy*, R. W. Baldwin and V. S. Byers (eds.), pp. 321–322 (Academic Press, 1985).

M. J. Embleton, "Targeting of Anti–Cancer Therapeutic Agents by Monoclonal Antibodies", *Biochemical Society Transactions*, 14, pp. 393–395 (615th Meeting, Belfast 1986).

N. Endo et al., "In Vitro Cytotoxicity of a Human Serum Albumin–Medicated Conjugate of Methotrexate with Anti–MM46 Monclonal Antibody", *Cancer Research*, 47, pp. 1076–1080 (Feb. 15th, 1987).

P. J. Fraker et al., "Protein and Cell Membrane Iodinations with a Sparingly Soluble Chloroamide, 1,3,4, 6–Tetrachloro–3a,6a–Diphenylglycoluril", *Biochem. Biophysical Comm.*, 80(4), pp. 849–857 (Feb.1978).

I. Hellström et al., "Antitumor Effects of L6, an IgG2a Antibody that Reacts with Most Human Carcinomas", *Pro.Natl.Acad.Sci.U.S.A.*, 83, pp. 7059–7063 (Sep. 1986).

I. Hellström et al., "Antibodies for Drug Delivery", *Controlled Drug Delivery* (2nd ed.), Robinson and Lee (eds.), pp. 638–642 (1987).

P. L. Ipata et al., "Baker's Yeast Cytosine Deaminase. Some Enzymic Properties and Allosteric Inhibition by Nucleosides and Nucleotides", *Biochemistry*, 10(23) pp. 4270–4276 (1971).

T. Katsuragi et al., "Affinity Chromatography of Cytosine Deaminase from *Escherichia coli* with Immobilized Pyrimidine Compounds", *Agric. Biol. Chem.*, 50(7), pp. 1713–1719 (1986).

J. M. Lambert et al., "Purified Immunotoxins That Are Reactive with Human Lymphoid Cells", *J. Biol. Chemistry* 260(22), pp. 12035–12041 (1985).

J. P. Mach et al., "Improvement of Colon Carcinoma Imaging: From Polyclonal Anti–CEA Antibodies and Static Photoscanning to Monoclonal Fab Fragments and ECT", *Monoclonal Antibodies for Cancer Detection and Therapy*, R. W. Baldwin et al (eds), pp. 53–64, Academic Press (1985).

R. B. McComb et al. (eds)., *Alkaline Phosphatase*, Plenum Press, Chapters 4, 5, 6 and 11 (New York 1979).

R. G. Melton et al., "In Vivo Localization of Carboxypeptidase G2:Antibody Conjugates in Human Colon Carcinoma Xenografts", from the Third International Conference on Monoclonal Antibody Immunoconjugates for Cancer Abstract #83, p. 110 (San Diego, Feb. 4–6, 1988).

S. Monfardini et al. (eds), *Manual of Cancer Chemotherapy*, Third Edition, UICC Technical Report Series, 56, Table of Contents, pp. 1–230 (Geneva 1981).

F. L. Moolten et al., "Antibodies Conjugated to Potent Cytotoxins as Specific Antitumor Agents", *Immunological Rev.*, 62, pp. 47–73 (1982).

K. Ohkawa et al., "Selective in Vitro and In Vivo Growth Inhibition Against Human Yolk Sac Tumor Cell Lines by Purified Antibody Against Human α–Fetoprotein Conjugated with Mitomycin C via Human Serum Albumin", Cancer Immunol. Immunother, 23, pp. 81–86 (1986).

C. W. Parker et al., "Enzymatic Activation and Trapping of Luminol–Substituted Peptides and Proteins. A Possible Means of Amplifying the Cytotoxicity of Anti–Tumor Antibodies", *Pro.Nat.Acad.Sci. USA*, 72(1), pp. 338–342 (1975).

G. W. Philpott et al., "Selective Iodination and Cytotoxicity of Tumor Cells with an Antibody–Enzyme Conjugate", *Surgery*, 74(1), pp. 51–58 (1973).

G. W. Philpott et al., "Selective Cytotoxicity of Hapten––Substituted Cells with an Antibody–Enzyme Conjugate", *The Journal of Immunology*, 111(3), pp. 921–929 (1973).

M. J. Robins et al., "Nucleic Acid Related Compounds. 16. Direct Fluorination of Uracil Nucleotides Using Trifluoromethyl Hypofluorite", *Can. J. Chem.*, 53, pp. 1302–1306 (1975).

G. F. Rowland et al., "Drug Localisation and Growth Inhibition Studies of Vindesine–Monoclonal Anti–CEA Conjugates in a human Tumour Xenograft", *Cancer Immunol Immunother*, 21, pp. 183–187 (1986).

F. Searle et al., "Antibody Carboxypeptidase G2 Conjugates as Anti–Tumor Agent", *Tumor Biology*, 6(4), p. 355 (1985).

F. Searle et al., "Carboxypeptiase G2 Conjugates with Localizing Anti–Tumour Antibodies: Potential Therapeutic Agents", *Tumor Biology*, 7(4), p. 320 (1986).

F. Searle et al., "The Potential of Carboxypeptidase G2 Antibody Conjugates as Anti–Tumour Agents. I. Preparation of Antihuman Chorionic Gonadotrophin–Carboxypeptidase G2 and Cytotoxicity of the Conjugate Against JAR Choriocarcinoma Cells In Vitro", *Br.J.Cancer*, 53, pp. 377–384 (1986).

W. T. Shearer et al., "Cytotoxicity with Antibody–Glucose Oxidase Conjugates Specific for a Human Colonic Cancer and Carcinoembryonic Antigen", *Int. J. Cancer*, 14, pp. 539–547 (1974).

V. J. Stella et al., "Prodrugs Do They Have Advantages in Clinical Practice?", *Drugs*, 29, pp. 455–473 (1985).

W. A. Thomas, "Prodrugs", *Biochemical Society Transactions*, 14, pp. 383–387 (615th Meeting, Belfast 1986).

P. E. Thorpe et al., "The Preparation and Cytotoxic Properties of Antibody–Toxin Conjugates", *Immunological Rev.*, 62, pp. 119–158 (1982).

P. E. Thorpe, "Antibody Carriers of Cytotoxic Agents in Cancer Therapy:A Review", *Monoclonal Antibodies '84 Biological and Clinical Applications*, A. Pinchera et al (eds), pp. 475–506 (1985).

E. S. Vitetta et al., "Redesigning Nature's Posions to Create Anti–Tumor Reagents", *Science*, 238, pp. 1098–1104 (1987).

M. Y. Yeh et al., "Cell Surface Antigens of Human Melanoma Identified by Monoclonal Antibody", *Proc.Natl.Acad.Sci.USA*, 76(6), pp. 2927–2931 (1979).

M. Y. Yeh et al., "Clonal Variation in Expression of a Human Melanoma Antigen Defined by a Monoclonal Antibody", *J. Immunol.*, 126(4), pp. 1312–1317 (1981).

*Primary Examiner*—Lila Feisee
*Attorney, Agent, or Firm*—Spencer & Frank

[57] ABSTRACT

A treatment for tumors to which antibody A5B7 binds is disclosed. A5B7 is a monoclonal antibody which binds to carcinoembryonic antigen. The treatment comprises administering to a host in need of such treatment an effective amount of a system which comprises: a conjugate comprising antibody A5B7 or a humanized version of A5B7 linked to an enzyme selected from the group consisting of carboxypeptidase G2 (CPG2), nitroreductase, a human enzyme, a non-human enzyme rendered non-immunogenic in man and a humanized catalytic antibody; and a prodrug convertible under the influence of the conjugate into a cytotoxic drug.

24 Claims, 2 Drawing Sheets

TREATMENT FOR TUMORS COMPRISING CONJUGATED ANTIBODY A5B7 AND A PRODRUG

This is a Division of application Ser. No. 07/642,301 filed Dec. 21, 1990 now abandoned.

THIS INVENTION relates to methods and systems for the control of neoplastic cell growth and is particularly concerned with methods and systems involving the localisation of cytotoxic agents at tumour sites.

In our earlier Patent Application PCT/GB88/00181 we disclose a two-component system which comprises (i) a first component (Component A-E) that is an antibody fragment capable of binding with a tumour associated antigen, the antibody fragment being bound to an enzyme capable of converting a prodrug into a cytotoxic drug;

(ii) a second or final component (Component PD) that is a prodrug convertible under the influence of the enzyme to a cytotoxic drug (CD).

In our earlier PCT Patent Application and in this present patent application, the word 'tumour' is to be understood as referring to all forms of neoplastic cell growth including carcinomas, sarcomas, lymphomas and leukaemias.

Our existing system is used to target cytotoxic prodrugs to the site of neoplastic cell growth. However, although this two-component system is useful in the control of tumours, the amount of first component that localises per gram of tumour in humans may be less than 0.1% the total amount of first component administered. A substantial proportion of the non-localised first component including active enzyme remains in the circulating blood. It is therefore desirable to reduce the amount of this freely circulating antibody-enzyme first component before administration of the prodrug so as to limit the formation of active drug in blood from where it would be carried to normal tissues. A similar problem arises when the first component is prepared from whole antibody.

The present invention provides methods for the removal from blood of residual conjugates of the enzyme or for inactivation of the enzyme in the residual first component with whole antibody or antibody fragment or equivalent component after the first component has localised at tumour sites.

The present invention is concerned with reducing problems arising in the clinical use of our above-mentioned two-component system from the presence in the patient of non-localised first component and permits further extension to be made to the nature of the first component.

The present invention provides a three-component system, for use in association with one another, in the treatment of malignant diseases comprising: a first component which is a substance or conjugation of substances characterised by (a) one or more molecular configurations that are complementary to molecular configurations associated with malignant cells, such that the first component tends to localise selectively at sites of malignant cells and (b) additionally by one or more catalytic sites; a second component which is able to bind to such part of the first component so as to inactivate the catalytic site of the first component and/or accelerates the clearance of the first component from the blood when the first and second components are administered clinically; a third component which is a substrate for the catalytic site on the first component, one of the end products of the catalysis being a substance which is more cytotoxic to maligant cells than the third component.

The clinically most useful form of the first component is a conjugate of an antibody or fragment thereof and an enzyme while the clinically most useful form of the third component is a prodrug convertible under the influence of the enzyme activity of the first component into a cytotoxic compound. The antibody will desirably be one recognising and binding preferentially to a tumour associated antigen and it will be apparent to those skilled in the art how to match the antigen associated with the particular tumour to be treated with the antibody or fragment to be used in the first component, how to match the cytotoxic compound to the tumour to be treated and how to match the prodrug to the enzyme activity of the first component.

As described in our above-mentioned copending International Patent Application PCT/GB88/00181 the prodrug can be benzoic acid mustard glutamide that converts to benzoic acid mustard [p-(bis-2-chloroethyl)amino]benzoic acid under the influence of a carboxypeptidase. However, the principles of this invention are equally applicable to other prodrugs releasing benzoic acid mustard or analogues thereof or other cytotoxic drugs using enzymes appropriate to the removal from the prodrug of the structural feature distinguishing the prodrug from the cytotoxic drug.

When antibody is used in the first component, it can be whole antibody or one of the antibody fragments, e.g. $F(ab')_2$ or other fragment as described in our above-mentioned earlier filed International Patent Application. The function of the antibody in the first component is to assist in the localisation of the first component in the region of the tumour to be treated and this function can also be fulfilled by substances other than antibodies, e.g. hormones or growth factors that have affinity to other tumour-associated compounds.

In one embodiment of the system of the invention the first component is a conjugate of an antibody to a tumour-associated antigen or a fragment thereof that includes the antigen binding site of the antibody, said antibody or fragment thereof being conjugated directly, or indirectly through a linking component, to an enzyme or to an antibody or antibody fragment with catalytic functions. In this case the conjugation can be effected by chemical bonding or by splicing together nucleic acid sequences that code at least for one or more antigen binding sites and one or more catalytic sites and such other sequences as are necessary to retain the vector function of the molecule and the catalytic function of the peptide when the gene product of the reconstructed nucleic acid sequence is expressed by eukaryotic or prokaryotic cells.

In a further embodiment, the antibody in the first component is bivalent and formed by bonding together two univalent antibody fragments, or by recombinant DNA techniques, one fragment having affinity for a tumour marker substance, the other having affinity for an enzyme. In such a case the conjugate can be formed either in vitro prior to administration or in vivo by first administering the bivalent antibody, allowing time for it to localise at tumour sites and then administering the enzyme for capture by the second arm of the antibody localised at tumour sites.

The antibody of the first component may be a human immunoglobulin, or fragment thereof, having antigen binding site(s) of human origin or having antigen binding site(s) of non-human species.

Reichmann L, Clark M, Waldmann H, and Winter G (Reshaping human antibodies for therapy—Nature 332: 323–327, 1988) shows that by genetic engineering techniques the antigen binding sites of a rodent monoclonal can be incorporated into human immunoglobulin fragments so that the immunogenicity of the molecule in the human subject is minimised. It has been shown that immunoglobulin-gene DNA can be manipulated so that the Fc portion of the antibody has been replaced with an active enzyme moiety (Neuberger M S, Williams G T, Fox R O—Nature 312: 604–608, 1984) and such genetically engineered constructs bearing one or more antigen binding sites and one or more enzyme active sites can be used in the present invention.

It has been observed that when monoclonal antibodies derived from one species are injected into another species the host antibody response may be (at least partially) directed at the idiotype of the injected monoclonal. (Rowe et al, IRCS Med Sci. 13: 936–7, 1985). Similarly, it is well-known that bacterial products, including enzymes, are immunogenic in mammalian species including man.

The present system will be most effective in man and suitable for repetitive use when the immunogenicity of a first component antibody-enzyme conjugate is minimised or if immune tolerance to such conjugates has been induced. This is likely to be achieved through genetic engineering methods since the production of monoclonals to specific antigens by human hybridomas has so far proved difficult to achieve consistently. It has been shown that the antigen binding site of a rodent monoclonal antibody can be incorporated into a human immunoglobulin framework (Reichmann et al, Nature 332: 323–327, 1988).

It has also been shown that antibodies can be produced which function as enzymes (Pollack S J et al, Science 234, 1570–1573, 1986) so the ultimate form of the antibody-enzyme conjugate may be a human immunoglobulin construct expressing one or more antigen binding sites characterised by peptide sequences of non-human origin and one or more catalytic sites.

With a 'humanised' antibody conjugated to a human enzyme or a non-human enzyme which has been rendered non-immunogenic in man, or a construct with both antigen binding and catalytic sites on a human immunoglobulin, the second component of our system will need to be directed at either the active site of the enzyme or at the idiotype of the antibody since a clearing antibody against the generality of human immunoglobulins would be unsuitable.

We have developed several different methods of removing what becomes the unwanted circulating first component after maximum localisation of the first component has occurred in the region of the tumour to be treated. The exact nature of the second component will depend upon the particular strategy to be used for removal of non-localised first component but the second component will always be one that either inactivates the catalytic site in the first component and/or accelerates its clearance from the blood.

According to one embodiment the second component is an antibody or fragment thereof having an affinity for an antigen binding site of an antibody of the first component or the active site of an enzyme of the first component or another constituent part of the first component.

According to a further embodiment the second component is one causing rapid loss of enzyme activity of the first component in plasma without incurring significant loss of enzyme activity from tumour sites.

According to a further embodiment the second component includes a sufficient number of covalently bound galactose residues or residues of other sugars such as lactose or mannose, so that it can bind enzyme in plasma but be removed together with the enzyme or antibody-enzyme conjugate from plasma by receptors for galactose or other sugars in the liver in a period of time such that the antibody does not, to any appreciable extent, enter the extravascular space of the tumour where it could inactivate tumour localised enzyme. In this case, galactose residues in the second component are either chemically added or exposed by removing terminal sialic acid residues.

Terminal sialic residues play a role in maintaining the presence of glycoproteins in the blood. Removal of terminal sialic acid by neuraminidase exposes proximal sugar residues such as galactose. Desialylated proteins are rapidly removed from the blood by receptors in liver and possibly other sites. (Morell et al, J. Biol. Chem. 246: 1461–1467, 1971).

Asialo human chorionic gonadotrophin was prepared by digesting 1 mg of a glycoprotein in 1 ml of 0.05M sodium acetate buffer, pH 5.6, containing 0.15M NaCl with 20 ug of neuraminidase (Sigma Type II from Vibro cholerae) at 37° for 30 minutes. The neuraminidase was then removed. Sialo and Asialo preparations were compared for clearance in A2G mice. T 1/2 for the sialyted hCG was in excess of 24 hours but T 1/2 for the desialyted form was <5 min.

A further embodiment of the invention is one wherein the first component is an antibody enzyme conjugate modified by addition of, or exposure of, additional galactose or other sugar residues, and is for administration in conjunction with an agent, such as asialofetuin, which has greater affinity for the corresponding sugar receptors which are involved in removing galactosylated or similar proteins from the blood, the asialofetuin blockade being maintained until satisfactory levels of conjugate have been attained in the tumour, then allowing the concentration of the conjugate in the plasma to fall before administering the third component.

This embodiment requires the addition of galactose residues to the antibody-enzyme conjugate by methods similar to those described for galactosylating the clearing antibody. Before administering the galactosylated conjugate the galactose receptors are blocked by an agent which binds more avidly to those receptors than the galactosylated conjugate. This results in maintenance of a high level of conjugate in the plasma until galactose receptors are again free to take up the conjugate.

Asialofetuin is a substance known to bind strongly to galactose receptors but other less immunogenic substances could be identified or developed for the same purpose.

A further embodiment of the invention is one wherein the second component is conjugated to a macromolecule such as a dextran, liposome, albumin microsphere or macroglobulin with a molecular weight in excess of 500,000 Daltons or a biodegradable particle such as a blood group 0 erythrocyte so that the second component is restrained from leaving the vascular compartment by virtue of the size of the conjugate.

A further embodiment of the invention is one wherein the second component is an antigen, hapten or protein construct bearing an epitope capable of binding with the first component to form complexes having accelerated clearance from plasma.

In a still futher modification of the system, the first component is covalently linked to biotin or derivatives of biotin, and the second component then comprises the biotin-binding glycoprotein avidin found in egg white, or streptavidin, itself optionally covalently linked to galactose.

Biotin may be conjugated to antibody or fragment thereof by reaction with a 10 molar excess of sulphosuccinimidyl 6-(biotinamido)hexanoate at pH 8.5 at 4° C. for 16 hours. The product is purified by chromatography on Sephadex G-25.

In all these cases, except for the procedure involving asialofetuin, the second component may be conjugated with a macromolecule or biologically degradable particle such that the additional component does not, to any appreciable extent, escape from the vascular compartment. The macromolecule may be optionally galactosylated.

Macromolecules to limit clearing component escaping from the vascular compartment are likely to be in excess of 500,000 Daltons and include carbohydrates such as dextrans, lipids as in liposomes or proteins such as in albumin microspheres or a macroglobulin. An example of a biodegradable particle for this purpose is an erythrocyte of blood group 0.

As an alternative to basing the first component on an antibody it may be based on a hormone or growth factor or substance other than an antibody and for which receptors capable of binding that substance exist on a tumour.

Tumours may express receptors for growth factor hormones and other metabolites such that these can be used as target sites for selective delivery. The corresponding growth factor, hormone, metabolite or genetic construct might then be used as the vector to carry an enzyme to tumour sites in a comparable fashion to antibody. There are literature examples of radiolabelled hormones, growth factors and metabolites localising in tumours (Krenning et al, Lancet i 242-244, 1989 (Somatostatin); Hattner et al, Am. J. Roentgenol. 143: 373-374, 1984) but in none of these were the vectors used to convey enzyme to tumour sites.

The enzyme part of the first component can be of human or non-human origin. The advantage of using an enzyme of human origin lies in avoiding or minimising the immunogenic effect of an enzyme of non-human origin. The disadvantage of an enzyme of human origin is the probability that the presence of enzyme in human tissues will activate the prodrug, thus releasing active drug at the non-tumour sites. However, it may be possible to identify certain human enzymes which are so distributed that this activation would not cause a serious problem. Also, inactivation of such enzymes in tissues might be achieved by using high affinity anti-enzyme antibody fragments which would be rapidly cleared from the plasma before giving the first component conjugate. Where the human enzyme is normally present in the plasma, this would activate prodrug in the plasma which would be highly disadvantageous and be liable to cause general toxic effects. Administration of an appropriately selected antibody or antibodies or fragments directed at the enzyme in the conjugate would however also have the effect of inactivating free, naturally recurring enzyme of the same type in the plasma. In the case of human phosphatases there are several different forms produced in different tissues but there is little evidence of specificity for substrates. There is also evidence that antibodies directed at one isotype of alkaline phosphatase may bind to other isotypes.

The immunogenicity of an enzyme of non-human origin may be reduced by modification of its amino acid sequence.

In order to render the antibody-enzyme conjugate less immunogenic, it can be modified by conjugation to polyethylene glycol or other polymers, e.g. by reaction with the cyanuric chloride derivative of methoxypolyethylene-glycol 5000. The resulting material may be employed directly, or may be pre-injected to render the host tolerant to further injections of the native conjugate. Reaction with synthetic copolymers of D-glutamine acid and d-lysine or with tripeptidyl-modified organic polymers comprising alternate D-glutamic acid and D-lysine on the exterior ends of the side chains can be predicted to depress the immunogenicity of the conjugate. See, for example, Abuchowsky A., van Es T., Palezuk N C, Davis F F—J. Biol. Chem. 252: (11), 3578–81, 1977, or Kawamura K, Igarishji, T, Fujii T., Kamasaki J., Wada, H., Kishimoto, S. Int. Arch. Allergy appl. Immunol. 76: 324–330, 1985.

To minimise clinical problems arising from the use of immunogenic antibody enzyme conjugates and immunogenic antibodies or avidin-like constructs, it is desirable to minimise or delay the production of host antibodies to xenospecific proteins by using immunosuppressive agents such as cyclosporin, cyclophosphamide, methotrexate, azathioprine etc., in order to provide sufficient time for the delivery of repeated treatments.

The ability of cyclosporin to prevent antimurine antibody responses by rabbits and in patients has been demonstrated. See, for example, Ledermann, J A. Begent, R H J. Bagshawe, K D. Br. J. Cancer, 58: 562–566, 1988, or Ledermann, J A. Begent, R H J. Riggs, S J. Searle, F. Glaser, M G, Green, A J. Dale, R G. Br. J. Cancer 58: 654–657, 1988.

In certain clinical conditions, it can be advantageous for the first component to be conjugated to a signal producing molecule such as a radioisotope suitable for scintigraphic imaging by gamma camera so as to confirm localisation of the first component at tumour sites.

Radiolabelling can be achieved with $^{125}I$ or $^{131}I$ with standard methods either using chloramine T (Greenwood F, Hunter W, Glover J S, Biochem. J. 89: 114–123, 1963, Fraker P J, Speck J C, Biochem. Biophys. Res. Comm. 80: 849–857, 1978), but other methods of iodination or radiolabelling with other isotopes such as indium or technetium can also be used. Such radiolabelled conjugates are generally used in clinical practice in amounts required for radioimmunolocalisation by immunoscintigraphy and would generally form only a small part of the administered conjugate.

Modern methods of analysis may be used in conjunction with a radiolabelled fraction of the conjugate to determine the concentration of the conjugate at target sites and non-target sites and thus help determine the optimum time for administration of the prodrug. (Riggs et al, Int. J. Cancer Supp. 2, 95–98, 1988, Dewhurst et al, (Abstract) Br. J. Cancer 1988).

The system of the present invention can include more than one type of first component and/or more than one type of second component and/or more than one type of third component. Heterogeneity in expression of target antigens and receptors on cells in tumours may require the use of more than one vector to carry enzyme to tumour sites. Multiple vectors may permit greater or more economical delivery of enzyme to tumour sites. It may also be advantageous to use more than one type of prodrug to generate a state equivalent to multidrug chemotherapy so as to reduce the risks of drug resistance and this in turn may require the use in treatment of more than one type of enzyme. These variations may in time require the use of more than one second component to achieve the required clearing of enzymes from plasma and other non-tumour sites.

The three components forming the system of the present invention are designed to be used in association with one another in a method of treatment of the human or animal body by therapy.

It is specifically designed for use in a method for the treatment of malignant diseases including carcinomas, sarcomas, lymphomas and leukaemias which comprises administering to a host in need of such treatment an effective amount of a system.

In such a method, the first component is administered first, the second component is administered subsequent to the first component after a time interval such that the first component has selectively localised at the site of malignant cells and the third component is administered subsequent to the second component after a time interval such that the concentration of the first component in the blood has reduced from its peak value.

The following Examples are given to illustrate various aspects of the invention.

EXAMPLE 1

This is to illustrate the inactivation of an active enzyme site by an antibody.

A monoclonal antibody (SB43) was produced by conventional methods following immunisation of the lymphocyte donor mouse with carboxypeptidase G$_2$. Microtitre plates were coated with three units per well of carboxypeptidase G$_2$ and incubated with supernatants from the hybridoma culture, and it was found that $^{125}$ Iodine labelled rabbit anti-mouse antibody bound to the coated wells with a 50% binding titre at a dilution of the supernatant of 1:800 in buffered solution. Assay of enzyme activity was assessed after 24 hours incubation at 37° C. in buffer containing a 1000-fold dilution of the antibody (hybridoma supernatant). Enzyme incubated with buffer alone for 24 hours retained most of its capacity to cleave methotrexate as shown by optical density measurements (54.1 carboxypeptidase units/ml initially falling to 40 units/ml activity after 24 hours). In the wells containing the antibody (hybridoma supernatant) the activity was reduced to 13.0 carboxypeptidase units/mi. The antibody alone had no effect on the optical density of methotrexate. These experiments show that the enzyme active site on the carboxypeptidase can be substantially inactivated by an antibody raised against the enzyme. Monoclonal antibodies to carboxypeptidase G$_2$, raised by the technique described above will only have a similar enzyme inhibiting property if they are directed at epitopes in or close to the active site of the enzyme.

EXAMPLE 2

Evidence for Localisation of Antibody-Enzyme Conjugate at Tumour Sites 1. 4 nude mice bearing LS174T human colon cancer xenografts on their L flanks were injected with A5B7 (Fab')$_2$ monoclonal antibody directed at carcinoembryonic antigen conjugated to carboxypeptidase G2 and labelled with $^{125}$I. The hybridoma which produces monoclonal antibody A5B7 has been deposited on Jul. 14, 1993 pursuant to the Budapest Treaty with the European Collection of Animal Cell cultures (ECACC) and has been given the accession number: ECACC 93071411. The address of the European Collection of Animal Cell Cultures is: ECACC, Public Health Laboratory Service, center for Applied Microbiology and Research, Porton Down, Salisbury, Witshire SP4OJG, United Kingdom. An immunoscintigraph taken after 48 hours confirms localisation of the conjugate at the tumour sites.

Similar results were obtained using the following conjugates:

2. A5B7 intact IgG—carboxypeptidase
3. A5B7-F(ab')$_2$—nitroreductase
4. SB10 (antiHCG)-F(ab')$_2$—carboxypeptidase 2. Methods of Conjugation of Antibody to Enzyme Conjugation of IgG or F(ab')$_2$ with carboxypeptidase was accomplished by mixing a maleimide derivative of the enzyme with a thiolated antibody.

1) Thiolation with S-acetylthioglycolic acid N-hydroxysuccinimide ester (SATA).

IgG or F(ab')$_2$ in 0.1M sodium phosphate buffer, pH 7.6, (containing 372 mg of EDTA/liter) at 1–2 mg/ml was treated with a 15 molar excess of SATA (made up 20 mg/ml in DMF) and left at about 20° C. for approximately 2 hours. The thiolated antibody was then passed down a column of Sephadex G-25 to remove excess SATA. The thiol was deacetylated by adding 0.1 volumes of 3.5% hydroxylamine, pH 7.5, prepared by adding disodium hydrogen phosphate to an aqueous solution of hydroxylamine hydrochloride.

2) Thiolation with N-succinimidyl 3-(2-pyridyldithio) propionate (SPDP).

IgG or F(ab')$_2$ in 0.2M sodium phosphate buffer, pH 8.6, at a concentration of 4 mg/ml was treated with a 15 molar excess of SPDP in ethanol and left at r.t. for 1 hour. Excess SPDP was removed on a column of Sephadex G-25 equilibrated in 0.1M sodium acetate buffer, pH 4.5. The pyridyldisulphide group was then reduced for 30 minutes with 50 ul/ml of 100 mM dithiothreitol and excess reducing agent removed by Sephadex G-25 gel filtration.

3) Derivatisation of carboxypeptidase.

Carboxypeptidase in 0.1M sodium phosphate buffer, pH 7.6 (containing 372 mg EDTA/liter) at 2 mg/2.5 ml was treated for 3 hours with a 15 molar excess of succinimidyl 4-(p-maleimidophenyl)butyrate (SMPB) dissolved in THF. The excess SMPB was removed by gel filtration on Sephadex G-25.

4) Conjugation

The derivatised enzyme was mixed with an equimolar amount of thiolated antibody and the progress of the conjugation monitored by gel filtration. When no further reaction was judged to take place the mixture was concentrated and the conjugate purified by gel filtration. Typical enzyme activities obtained were 150–200 units/mg of conjugate.

EXAMPLE 3

Evidence That SB43 Binds to Carboxypeptidase G2 In Vitro

Microtitre wells were coated with carboxypeptidase G2 and monoclonal antibodies SB43 (raised to carboxypeptidase G2) and SB10 (raised to human chorionic gonadotrophin) were added in dilution and incubated before aspiration. $^{125}$I anti-mouse IgG was then added and incubated for 30 minutes followed by aspiration and washing. The wells were cut out and counted in a gamma counter. The results set out below show no significant binding of SB10 to the carboxypeptidase coated wells but all dilutions of SB43 used showed high counts indicating binding to the carboxypeptidase. SB43 modified by addition of galactose moieties was included a similar dilution and showed similar binding to unmodified SB43.

The microtitre plate was coated with 0.1 microg. $CPG_2$ per well and incubated overnight with SB43. The $^{125}$I-mouse IgG was then introduced, the plate incubated for 1 hour, washed and radio-counted.

| SAMPLE | TIME | COUNTS (1) | CPM (1) | % CV | |
|---|---|---|---|---|---|
| 1 | 30 | 1092 | 2171.4 | 3.1 | (Negative Control-SB10-Anti-hCG) |
| 2 | 30 | 805 | 1588.6 | 3.6 | (Negative Control-SB10-Anti-hCG) |
| 3 | 30 | 16428 | 33278.0 | .8 | SB43 × 20 |
| 4 | 30 | 23339 | 47302.9 | .7 | " |
| 5 | 30 | 22020 | 44679.3 | .7 | SB43 × 100 |
| 6 | 30 | 22096 | 44833.8 | .7 | " |
| 7 | 30 | 8437 | 16873.4 | 1.1 | SB43 × 1000 |
| 8 | 30 | 7671 | 15336.8 | 1.1 | " |
| 9 | 30 | 15411 | 31052.2 | .8 | SB433-Gal-10 × 20 |
| 10 | 30 | 15418 | 31066.3 | .8 | " |

EXAMPLE 4

Evidence That SB43 Inactivates/Clears Ab-E-Conjugate In Vivo From Plasma

The level of carboxypeptidase G2 activity in plasma can be monitored by observing the hydrolytic cleavage of methotrexate, a folic acid analogue, to pteroates and L-glutamate. When a conjugate of A5B7-F(ab')$_2$-carboxypeptidase G2 (25 enzyme units) was injected intravenously and plasma samples obtained 20 hours later significant hydrolysis of methotrexate was observed equivalent to 1.12 to 1.45 enzyme units/ml as shown by the steps of the spectrophotometric print-out.

Mice which were injected with galactosylated anti-carboxypeptidase (SB43-Gal 10) 19 hours after A5B7F(ab')$_2$-CPG2 and plasma taken 5 minutes and 15 minutes later caused no significant hydrolysis of methotrexate showing that the enzyme had been inactivated and/or cleared from the plasma.

EXAMPLE 5

Biotinylation of Antibody-Enzyme Conjugate

Carboxypeptidase G2 (44.4 mg) in 0.05M sodium bicarbonate buffer, pH 8.5 (1.5 ml) was mixed with sulphosuccinimidyl 1-6-(biotinamide) hexanoate (292 ug in 73 ul of buffer and left at room temperature for 3 hours. The enzyme was then separated on Sephadex G-25 equilibrated in 0.15M sodium phosphate buffer pH 7.6, containing 372 mg EDTA/liter and the volume adjusted to 2.5 ml. The biotinylated enzyme was then treated for 3 hours with a 15 molar excess of succinimidyl 4-(p-maleimido phenyl)butyrate (SMPB) dissolved in tetrahydrofuran and the excess SMPB removed by gel filtration on Sephadex G25. The derivatised enzyme was then conjugated to thiolated F(ab')$_2$ fragment of the A5B7 antibody as described in Example 2.

Affinity purified avidin was used as obtained from Sigma Ltd., 10–15 units/mg protein. Mice received 20 ug of biotinylated A5B7-carboxypeptidase G2 conjugate followed after one hour by avidin in the dose range 20–500 ug. Rapid clearance of the enzyme activity in plasma was observed comparable to that observed with SB43 monoclonal antibody in Example 4.

EXAMPLE 6

IgG class immunoglobulins carrying different specificities on their two binding sites can be made by a fusion technique employing hybridomas producing different antibodies (Milstein C & Cuello A C. Nature 305: 537–540, 1983; Sfaerz U D & Bevan M J. Proc. Nat. Acad. Sci. USA 83: 1453–1457, 1986) or by chemical conjugation of univalent preparations of each of the antibodies required as used here. F(ab')$_2$ fragments of monoclonals SB10 (anti-human chorionic gonadotrophin (anti-hCG)) and A5B7 (anti-carcinoembryonic antigen, (anti-CEA)) were reduced in the presence of arsenite. F(ab')$_2$ fragment (20 mg) in 0.1M sodium phosphate buffer pH 7.6 (10 ml) was mixed with sodium arsenite (12.4 mg) EDTA (3.72 mg) and 2-mercaptoethylamine (1.13 mg) and left at room temperature. Solid 5,5'-dithio-bis-(2-nitrobenzoic acid) (19.8 mg) was added and the mixture left at about 20° C. for 18 hours. The thionitrobenzoate modified Fab' (TNB derivative) was purified by gel filtration on Sephadex G-25 with a yield of approximately 70% based on protein recovery.

The TNB derivative of anti-CEA (4.8 mg) in 5 ml of 0.1M sodium phosphate buffer, pH 6.8, containing 1 mM EDTA was treated for 30 minutes with mercaptoethylamine to give a final concentration of 10 mM. The reduced TNB-anti-CEA Fab' was then purified by gel filtration on Sephadex G-25 equilibrated in 0.1M sodium phosphate buffer pH 7.0, containing 1 mM EDTA. The reduced TNB-anti-CEA Fab' was then incubated with 4.9 mg (5 ml) of TNB derivative of anti-hCG for 16 hours and the formation of bispecific antibody monitored by gel filtration on a Superose S-12 column (Pharmacia). The yield was 20% based on protein after purification of the bispecific antibody on the Superose S-12 column. The ability of this $^{125}$I labelled biospecific antibody to function in vivo and bind to its corresponding antigen was demonstrated by injection into nude mice bearing either CEA producing LS174T tumours or hCG producing CC3 tumours. At 20 hours post-injection mean tumour to organ ratios were:

| anti CEA/anti hCG | non-specific F(ab')$_2$ |
|---|---|
| blood 2.9 | 0.6 |
| liver 3.9 | 1.9 |
| kidney 1.8 | 1.2 |
| lung 3.2 | 1.2 |
| spleen 6 | 3.0 |
| colon 9 | 5.3 |

(Conjugation of A5B7 and SB43 (anticarboxypeptidase) has not yet been performed but above experiment demonstrates retention of binding site function).

EXAMPLE 7

Method for Galactosylation

Cyanomethyl 2,3,4,6-tetra-0-acetyl-1-thio-b-D) galactopyranoside (400 mg) in anhydrous methanol (10 ml) was treated with 5.4 mg of sodium methoxide in 1 ml of anhydrous methanol at about 20° C. for 48 hours. A stock solution of IgG in 0.25M sodium borate buffer, pH 8.5 at 1.3 mg/ml was prepared. Since the number of galactose residues conjugated to IgG was not determined, a unitage was adopted corresponding to the number of microliters of the activated galactose derivative added to 200 ug of IgG at a concentration of 1.3 mg/ml.

Figure 1A:
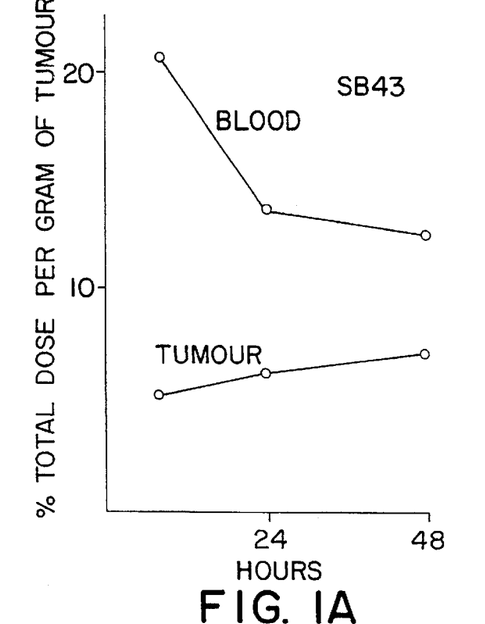
FIG. 1A and FIG. 1B show blood and tumour levels up to 48 hours after injection of monoclonal SB43 (anti-carboxypeptidase). A, native form; B, galactosylated form.
Figure 1B:
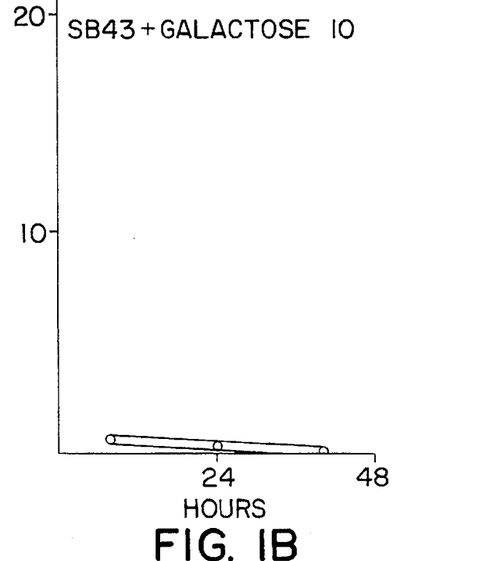

Aliquots of the activated galactose derivative (e.g. 300, 80, 40, 10, 5 and 2 ul) were dispensed into 3 ml glass ampoules and evaporated to a glassy residue in a stream of nitrogen under vacuum. 200 micrograms of IgG (153 ul of stock solution) were added to each aliquot and mixed until the residue was dissolved. After 2 hours at about 20° C. the solution was dialysed against 3 changes of PBS (phosphate buffer saline). Tests were performed to determine what level of galactosylation gave the most effective results. It was found that, in terms of the unitage defined above, 10 ul of the activated glactose derivative added to 200 ug of IgG gave the most satisfactory results. FIG. 1A and FIG. 1B shows blood and tumour levels up to 48 hours after injection of monoclonal SB43 (anti-carboxypeptidase). A, native form; B, galactosylated form. Further studies were performed, each in groups of 4 mice, bearing LS174T tumours and receiving A5B7 F(ab')2-CP (carboxypeptidase G2) conjugate followed after 24 hours by SB43 (anti-carboxypeptidase) galactosylated to the 10 ul level (as defined previously) or with saline as control followed one hour later by the bis-chloro benzoic acid mustard prodrug, 4-[bis-(2-chloroethyl)amino]-benzoic acid glutamide. Mice were killed at intervals following administration of the prodrug, the tissues extracted and prodrug and active drug levels were measured by HPLC methods.

Figure 1C:
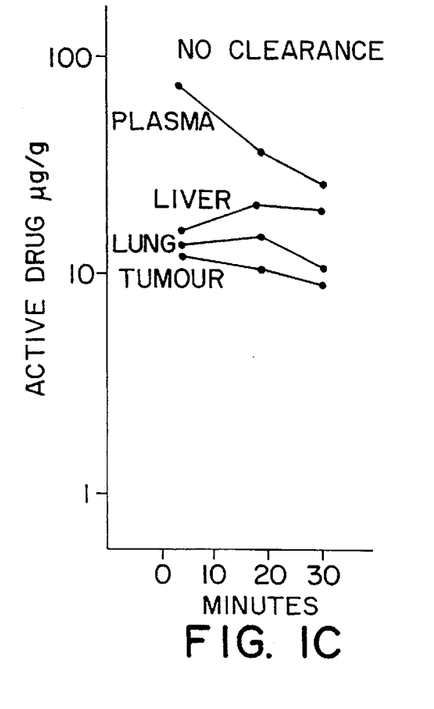
FIG. 1C and FIG. 1D show the levels of active drug in various tissues in mice which have not received SB43-Gal 10 clearing antibody with those that had.
Figure 1D:
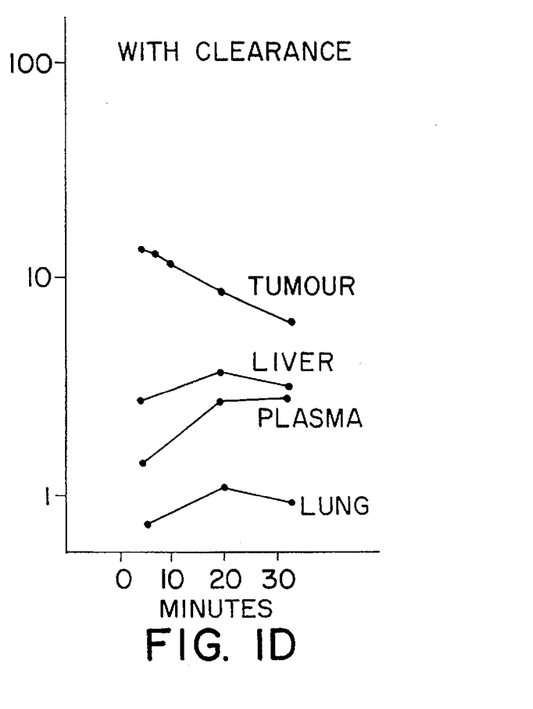

FIG. 1C shows the levels of active drug in various tissues in mice which had not received SB43-Gal 10 clearing antibody with those that had. In the absence of SB43-Gal 10 clearing antibody, levels of active drug were significantly lower than those found in liver and lung but in animals receiving the SB43-Gal 10 clearing antibody tumour levels were higher than in any other tissue.

As part of the same experiment two groups of mice, one with and one without SB43-Gal 10, were killed without receiving the prodrug. The tissues were extracted and tested for ability to convert prodrug to active drug in vitro. The results are shown in the Table and expressed as percentage of injected dose of carboxypeptidase per gram of tissue.

| In vivo admin | Carboxypeptidase G2% i.v. dose per gram of tissue at 48 hours | | |
|---|---|---|---|
| | Tumour | Plasma | T/P |
| Ab-CPG2 | 8.1(+0.69) | 0.22 | 36 |
| AB-CPG2 | 7.2(+1.42) | 0.026 | 277 |

+Gal 10 antiCPG2 24 hours later

EXAMPLE 8

Where the antigen corresponding to an intravenously administered antibody is present in the blood, antigen-antibody complexes form and these accelerate clearance of the antibody from the circulation into the reticuloendothelial cells. Accelerated clearance of anti-hCG antibodies W14 and SB10 occurs when these are injected into nude mice bearing CC3 hCG secreting tumours when compared with A5B7 anti-CEA antibody in LS174T bearing mice which express CEA on LS174T cell membranes but do not secrete CEA into the blood.

Figure 2A:
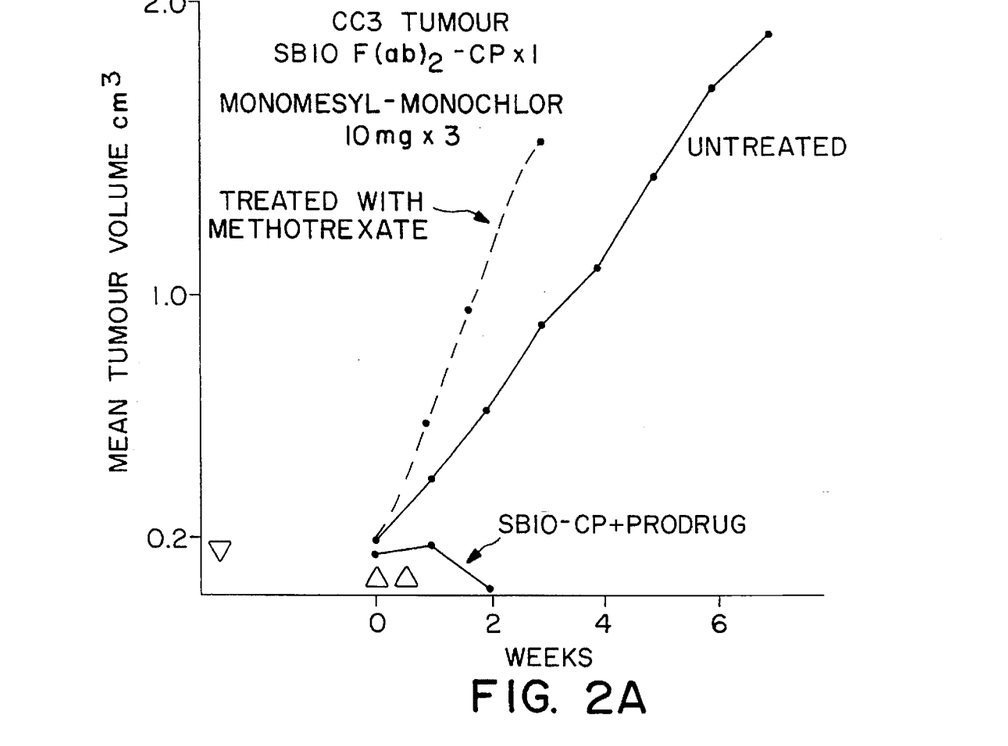
FIG. 2A shows the result of administering SB10 F(ab')$_2$-CP (50 units CP) intravenously to 6 CC3 bearing nude mice, followed by the first of three injections of monomesyl monochloro benzoic acid mustard prodrug 4-[(2-chloroethyl)mesylamino]benzoic acid glutamide.

FIG. 2A shows the result of administering SB10 F(ab')$_2$-CP (50 units CP) intravenously to 6 CC3 bearing nude mice, followed by the first of three injections (10 mg each) of the monomesyl monochloro benzoic acid mustard prodrug 4-[(2-chloroethyl)mesylamino]benzoic acid glutamide, the second given at 56 hours and the third at 72 hours. After 2 weeks the tumour was no longer detectable and the mice remain tumour free at 12 weeks. The growth of CC3 tumours in 6 untreated mice is also shown.

Attempts to introduce the prodrug into LS174T bearing mice before 120 hours after administration of A5B7 F(ab')$_2$-CP 50 units resulted in death of the animals and this was shown to be due to persisting enzyme activity in the blood.

Figure 2B:
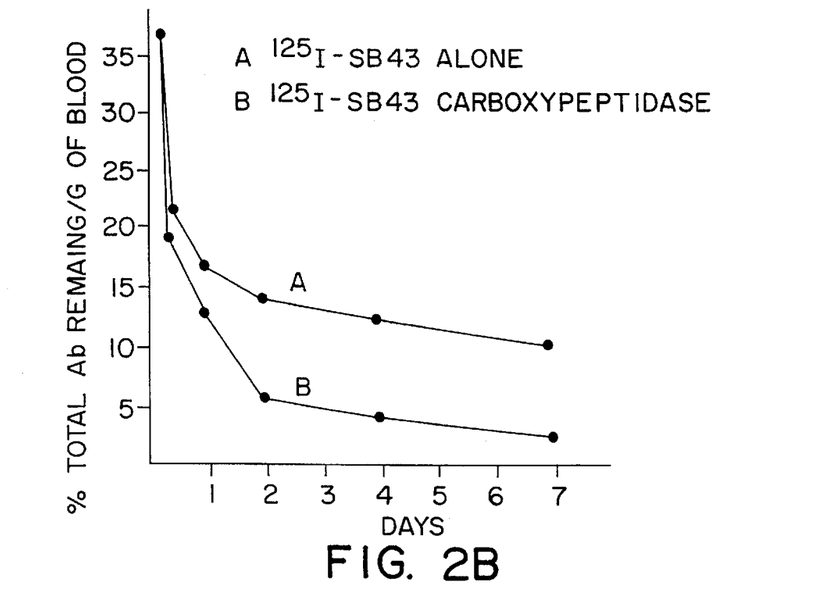
FIG. 2B shows accelerated clearance of 20 μg monoclonal $^{125}$I-SB43 anticarboxypeptidase from the blood of A2G mice when 77 μg of the corresponding antigen, carboxypeptidase G2, was administered 1 hour later compared with controls which did not receive the antigen.

FIG. 2B shows accelerated clearance of 20 ug monoclonal $^{125}$I-SB43 anticarboxypeptidase from the blood of A2G mice when 77 ug of the corresponding antigen, carboxypeptidase G2, was administered 1 hour later compared with controls which did not receive the antigen.

These data indicate that accelerated clearance of an administered antibody can be achieved by administration of a substance expressing the epitope corresponding to the binding site of the antibody.

EXAMPLE 9

Conjugation of TCK9 Human Albumin Microspheres to SB43

1 mg of TCK9 human polyalbumin microspheres were derivatised with a 12.5M excess of sulpho-MBS (based on monomeric unit of 66 Kd) in a total of 1 ml phosphate buffer pH 7.8 for 2 hours at about 20° C. The mixture was centrifuged at 3000 rpm for 3 minutes and resuspended in 1 ml of buffer, and rewashed once more. 1.5 mg of $^{125}$I labelled SB43 was thiolated by 20M excess of SPDP, according to manufacturers (Pharmacia) instructions, at about 20° C. The derivatised microspheres were centrifuged at 3000 rpm for 3 minutes, and then resuspended in the thiolated SB43 solution, the conjugation was carried out by incubating the mixture at 4° C. for 72 hours.

The antibody polyalbumin conjugate was separated from the reaction mixture by centrifuging at 13000 rpm (MSE Micro centaur) for 2 minutes; the pellet was resuspended in 250 ul of sterile saline for use.

EXAMPLE 10

Asialofetuin was given intravenously at time zero and again at 120 minutes to mice bearing LS174T xenografts. $^{125}$I-A5B7-galactosylated to 10 units was administered at time +5 minutes. Mice were killed at intervals and tissues excised and radioactivity levels counted. At 24 hours the tumour to blood ratio was 27.8:1 and the tumour to liver ratio 4.2:1. All other tissues showed even more favourable ratios. It should be recognised that whereas enzyme taken up by liver is rapidly inactivated, radioactivity persists in the organ.

We claim:

1. A conjugate comprising A5B7 antibody and an enzyme selected from the group consisting of carboxypeptidase G2 enzyme and nitroreductase.

2. A conjugate according to claim 1 wherein the antibody lacks an Fc portion.

3. A conjugate according to claim 1 wherein the antibody is a F(ab')2 structure.

4. A conjugate according to claim 1 wherein the antibody is linked to the enzyme via a continuous polypeptide linkage.

5. A conjugate according to claim 1 wherein the antibody is humanized.

6. A two component system which comprises:

i) a conjugate as defined in claim 1; and ii) a prodrug convertible under the influence of the conjugate into a cytotoxic drug.

7. A two component system which comprises:

i) a conjugate as defined in claim 1; and ii) a mustard prodrug convertible under the influence of the conjugate into a cytotoxic drug.

8. A pharmaceutical composition comprising a conjugate as defined in claim 1.

9. A conjugate comprising A5B7 antibody and a member of the group consisting of a human enzyme, a non-human enzyme rendered non-immunogenic in man and a humanized catalytic antibody.

10. A conjugate according to claim 9 wherein the antibody lacks an Fc portion.

11. A conjugate according to claim 9 wherein the antibody is a F(ab')2 structure.

12. A conjugate according to claim 9 wherein the antibody is linked to the enzyme via a continuous polypeptide linkage.

13. A conjugate according to claim 9 wherein the antibody is humanized.

14. A two component system which comprises:

i) a conjugate as defined in claim 9; and ii) a prodrug convertible under the influence of the conjugate into a cytotoxic drug.

15. A two component system which comprises:

i) a conjugate as defined in claim 9; and ii) a mustard prodrug convertible under the influence of the conjugate into a cytotoxic drug.

16. A pharmaceutical composition comprising a conjugate as defined in claim 9.

17. A conjugate comprising A5B7 antibody and carboxypeptidase G2 enzyme.

18. A conjugate according to claim 17 wherein the antibody lacks an Fc portion.

19. A conjugate according to claim 17 wherein the antibody is a F(ab')2 structure.

20. A conjugate according to claim 17 wherein the antibody is linked to the enzyme via a continuous polypeptide linkage.

21. A conjugate according to claim 17 wherein the antibody is humanized.

22. A two component system which comprises:

i) a conjugate as defined in claim 17; and ii) a prodrug convertible under the influence of the conjugate into a cytotoxic drug.

23. A two component system which comprises:

i) a conjugate as defined in claim 17; and ii) a mustard prodrug convertible under the influence of the conjugate into a cytotoxic drug.

24. A pharmaceutical composition comprising a conjugate as defined in claim 17.

* * * * *